(12) United States Patent
Bundle et al.

(10) Patent No.: US 7,722,890 B2
(45) Date of Patent: May 25, 2010

(54) **SYNTHETIC ANTI-*CANDIDA ALBICANS* OLIGOSACCHARIDE BASED VACCINES**

(75) Inventors: David R. Bundle, Edmonton (CA); Mark Nitz, Cambridge, MA (US); Jim E. Cutler, New Orleans, LA (US)

(73) Assignee: Theracarb, Inc., Calgary, Alberta (CA)

( * ) Notice: Subject to any disclaimer, the term of this patent is extended or adjusted under 35 U.S.C. 154(b) by 765 days.

(21) Appl. No.: 10/512,216

(22) PCT Filed: Apr. 25, 2003

(86) PCT No.: PCT/CA03/00614

§ 371 (c)(1),
(2), (4) Date: Jul. 22, 2005

(87) PCT Pub. No.: WO03/090787

PCT Pub. Date: Nov. 6, 2003

(65) Prior Publication Data

US 2006/0058506 A1 Mar. 16, 2006

Related U.S. Application Data

(60) Provisional application No. 60/376,016, filed on Apr. 25, 2002.

(51) Int. Cl.
*A61K 39/00* (2006.01)
(52) U.S. Cl. .................................. 424/274.1
(58) Field of Classification Search ........................ None
See application file for complete search history.

(56) References Cited

U.S. PATENT DOCUMENTS

| | | | |
|---|---|---|---|
| 5,578,309 A | | 11/1996 | Cutler et al. |
| 5,650,234 A | * | 7/1997 | Dolence et al. ............. 428/447 |
| 6,248,329 B1 | * | 6/2001 | Chandrashekar et al. . 424/191.1 |
| 6,630,146 B2 | | 10/2003 | Cutler et al. |
| 6,632,437 B1 | * | 10/2003 | Schneerson et al. ...... 424/193.1 |

OTHER PUBLICATIONS

Nitz et al The Unique Solution Structure and Immunochemistry of the *Candida albicans* b-1,2-Mannopyranan Cell Wall Antigens Journal of Biological Chemistry. No. 5 pp. 3440-3446 (2002) Epub Nov. 7, 2001.*
Nitz et al. (2001) Journal of Organic Chemistry vol. 66. No. 5 pp. 8411-8423.*
Nitz et al. (2002) Epub Nov. 7, 2001 Journal of Biological Chemistry. No. 5 pp. 3440-3446.*
Nitz et al. (2000) Organic Letters Jun. 7, 2000 vol. 2 No. 19 pp. 2939-2942.*
Joaquin et al Chem. Eur. J. 1999 5 No. 5 pp. 1512-1525.*
Kamath et al 1996 Glycoconj J. Apr. 1996;13(2):315-9.*
Wilstermann Lund 1997 Dissertation abstract..*
(Chapter 29 of Vaccines, Plotkin, et al. (eds) WB Saunders, Philadelphia, 1998, especially p. 571, paragraph 2) pp. 568-575.*
Bowie et al (Science, 1990, 247:1306-1310).*
Greenspan et al. (Nature Biotechnology 7: 936-937, 1999).*
See Cripps et al Current Opinion in Immunology 2002, 14 pp. 553-557.*
Nitz et al Journal of Biological Chemistry 2002 No. 5 pp. 3440-3446.*
Shibata et al 1992 Biochemistry vol. 31 pp. 5680-5686.*
Gattuso et al 1998 Chem Rev. pp. 1919-1958.*
Nitz et al. (2000) Organic Letters Jun. 7, 2000 vol. 2 No. 19 pp. 2939-2942.*
Nitz et al. "Synthesis of Di- to Hexasaccharide 1,2-Linked β-Mannopyranan Oligomers, a Terminal S-Linked tetrasaccharide Congener and the Corresponding BSA Glycoconjugates" *J. Org. Chem.* 66:8411-8423 (2001).
Nitz et al. "The Unique Solution Structure and Immunochemistry of the *Candida albicans* β-1,2-Mannopyranan Cell Wall Antigens" *J. Biol. Chem.* 277:3440-3446 (2002).
Han et al. "A Vaccine and Monoclonal Antibodies That Enhance Mouse Resistance to *Candida albicans* Vaginal Infection" *Infect. Immun.* 66:5771-5776 (1998).
Kanabe et al. "Evidence for Adhesin Activity in the Acid-Stable Moiety of the Phosphomannoprotein Cell Wall Complex of *Candida albicans*" *Invect. Immun.* 62:1662-1668 (1994).
Rodriguez et al. "Aminooxy-, Hydrazide-, and Thiosemicarbazide-Functionalized Saccharides: Versatile Reagents for Glycoconjugate Synthesis" *J. Org. Chem* 63:7134-7135 (1998).
Nitz et al. "Synthesis of a β1,2-Mannopyranosyl Tetrasaccharide Found in the Phosphomannan Antigen of *Candida albicans*" *Org. Letters* 2:2939-2942 (2000).
Jouault et al. "Differential Humoral Response against α- and β-Linked Mannose Residues Associated with Tissue Invasion by *Candida albicans*" *Clin. Diag. Lab. Immun.* 4:328-333 (1997).

(Continued)

*Primary Examiner*—Robert B Mondesi
*Assistant Examiner*—Nina A Archie
(74) *Attorney, Agent, or Firm*—Swiss Tanner, P.C.

(57) ABSTRACT

The present invention provides methods of making and using immunogenic oligosaccharide compositions comprising native O-linked and S-linked oligosaccharides coupled to a protein carrier, wherein the resultant conjugate elicits a protectively immunogenic response. These compositions may be useful in vaccines against pathogenic *Candida* species.

11 Claims, 9 Drawing Sheets

OTHER PUBLICATIONS

Han et al. "Antibody Response that Protects against Disseminated Candidiasis" *Infect. Immun.* 63:2714-2719 (1995).

Kabat, Elvin A. "Introduction—structures of some determinants of antigenic specificity" *Federation Proc.* 21:692-693 (1962).

Li, et al. "Chemical Definitino of an Epitope/Adhesin Molecule on *Candida albicans*" *J. of Biological Chemistry* 268:18293-18299 (1993).

Nitz, Mark "Synthesis of *Trichinella spiralis* and *Candida albicans* Antigens, containing β-Mannopyranosyl Epitopes, their Conformation and Immunochemistry" *University of Alberta, Department of Chemistry*, Edmonton, Alberta Fall 2001.

Casadevall et al. "Antibody and/or cell-mediated immunity, protective mechanisms in fungal disease: an ongoing dilemma or an unnecessary dispute?" *Med. Mycol.* 36, Suppl. 1:95-105 (1998).

Beck-Sangue et al. "Secular Trends in the Epidemiology of Nosocomial Fungal Infections in the United States, 1980-1990" *J. Infect. Dis.* 167:1247-1251 (1993).

Han et al. "Assessment of a Mouse Model of Neutropenia and the effect of an Anti-Candidiasis Monoclonal Antibody in These Animals" *J. Infect. Dis.* 175:1169-1175 (1997).

Levitz, Stuart M. "Overview of Host Defenses in Fungal Infection" *Clin. Infect. Dis.* 14(Suppl 1):S37-42 (1992).

Shibata et al. "Characterization of Phosphomannan-Protein Complexes Isolated from Viable Cells of Yeast and Mycelial Forms of *Candida albicans* NIH B-792 Strain by the Action of Zymolyase-100T" *Arch. Biochem. Biophys.* 251:697-708 (1986).

Landmann et al. "Failure of All Antifungal Therapy for Infection Due to *Candida albicans*: A New AIDS-Related Problem?" *Clin. Infect. Dis.* 26:183-184 (1998).

Kabat, Elvin A. "The nature of an Antigen Determinant" *J. of Immunol.* 97:1-11 (1966).

Bousquet et al. "Synthesis and Immunostimulating Activity of a Thioglycolipopeptide Glycomimetic as a Potential Anti-Cancer Vaccine Derived from TN Antigen" *J. Carbo. Chem.* 19:527-54141 (2000).

Barresi et al. "Synthesis of β-D-Mannose Containing Oligosaccharides" Harwood Academic Publishers: Amsterdam 251-276 (1996).

Shibata et al. "Structural Analysis of Phospho-$_D$-Mannan-Protein Complexes Isolated from Yeast and Mold Form Cells of *Candida albicans* NIH A-207 Serotype A Strain" *Carbohydrate Research* 187:239-253 (1989).

Han et al. "Protection against Candidiasis by an Immunoglobulin G3 (IgG3) Monoclonal Antibody Specific for the Same Mannotriose as an IgM Protective Antibody" *Infect. Immun.* 68:P1649-1654 (2000).

Han et al. "Complement Is Essential for Protection by an IgM and an IgG3 Monoclonal Antibody Against Experimental, Hematogenously Disseminated Candidiasis" *J. Immunol.I* 167:1550-1557 (2001).

Han et al. "Biochemical Characterization of *Candida albicans* Epitopes That Can Elicit Protective and Nonprotective Antibodies" *Infect. Ummun.* 65:4100-4107 (1997).

Trinel et al. "the *Candida albicans* Phospholipomannan Is a Family of Glycolipids Presenting Phosphoinositolmannosides with Long Linear Chains of β-1,2-Linked Mannose Residues" *J. Biol. Chem.* 274:30520-30526 (1999).

Trinel et al. "Definitive chemical evidence for the constitutive ability of *Candida albicans* serotype A strains to synthesize β-1,2 linked aligomannosides containing up to 14 mannose residues" *FEBS* 416:203-206 (1997).

Han, et al. "*Candida albicans* Mannan Extract-Protein Conjugates Induce a Protective Immune Response against Experimental Candidiasis" *J. Infect. Dis.* 179:1477-1484 (1999).

Gridley et al. "Recent advances in the construction of β-D-mannose of β-D-mannosamine linkages" *J. Chem. Soc. Perking Trans*:1 1471-1491 (2000).

Lergenmüller, et al. "On the Sterochemistry of Tethered ntermediates in *p*-Methoxybenzyl-Assisted β-Mannosylation" *Eur. J. Org. Chem.* 1367-1376 (1999).

Crich et al. "Direct Formation of β-Mannopyranosides and Other Hindered Glycosides from Thioglycosides" *J. Am. Chem. Soc.* 120:435-436 (1998).

Kabat "Antigenic determinants of dextrans and blood group substances" *Federation Proceedings* 21:694-701 (1962).

Kabat. "Introduction—structures of some determinants of antigenic specificity" *Federation Proc.* 21:692-693 (1962).

\* cited by examiner

A portion of *Candida albicans* N-linked mannan, glycan chain lengths vary.

Synthesis of di through hexasaccharide (1→2)-β-D-mannopyranan oligomers. a) 2, AgOTf, DtBMP, (CH₃)₃CCN/CH₂Cl₂; b) L-Selectride, THF.

Deprotection of (1→2)-β-D-mannopyranan oligomers. a) 2-aminoethanethiol hyrochloride, MeOH/CH$_2$Cl$_2$, hv 365 nm; b) Na/NH$_3$, tBuOH, THF; c) NH$_2$NH$_2$.H$_2$O, EtOH/THF; d) Pd/C, H$_2$, EtOH.

Synthesis of the thioglyoside mimetic of (1→2)-β-D-mannopyranotetraose. a) TMSOTf, CH$_2$Cl$_2$, 76%; b) MeONa, MeOH/THF, 94%; c)Tf$_2$O, pyridine, 89%; d) KSAc, DMF, 63%; e) Hydrazine hydrate, cyclohexene, EtOH/THF, 89%; f) i. 2, lutidine, CH$_2$Cl$_2$, ii. L-Selectride, THF, 49%.

28 R¹=pClBn, R²= Bn, R³= CHPh, R⁴=All
29 R¹=pClBn, R²= Bn, R³= CHPh, R⁴=(CH$_2$)$_3$S(CH$_2$)$_2$NH$_2$
30 R¹=pClBn, R²= Bn, R³= CHPh, R⁴=(CH$_2$)$_2$CH$_3$
31 R¹, R², R³= H, R⁴=(CH$_2$)$_3$S(CH$_2$)$_2$NH$_2$
32 R¹, R², R³= H, R⁴=(CH$_2$)$_2$CH$_3$

Deprotection of the thioglyoside mimetic of (1→2)-β-D-Mannopyranotetraose. a) 2 aminoethanethiol hydrochloride, MeOH/CH$_2$Cl$_2$, hν 365 nm; b) NH$_2$NH$_2$.H$_2$O, EtOH/THF; c) Na/NH$_3$, tBuOH, THF.

| 13 R = disaccharide | 33 R = disaccharide | 38 R = disaccharide |
| 14 R = trisaccharide | 34 R = trisaccharide | 39 R = trisaccharide |
| 15 R = tetrasaccharide | 35 R = tetrasaccharide | 40 R = tetrasaccharide |
| 16 R = hexasaccharide | 36 R = hexasaccharide | 41 R = hexasaccharide |
| 31 R = thio-tetrasaccharide | 37 R = thio-tetrasaccharide | 42 R = thio-tetrasaccharide |

Synthesis of oligomannoside squarate conjugates

Figure 7

Inhibition of the binding of IgM monoclonal antibody B6.1 to *C. albicans* mannan extract by propyl mannosides (17, 18, 19, 32, 21)

Inhibition of binding of IgG monoclonal antibody to C. albicans mannan extract with propyl mannosides (17, 18, 19, 32, 21). The origin of the flattened the binding curve for the disaccharide is unknown

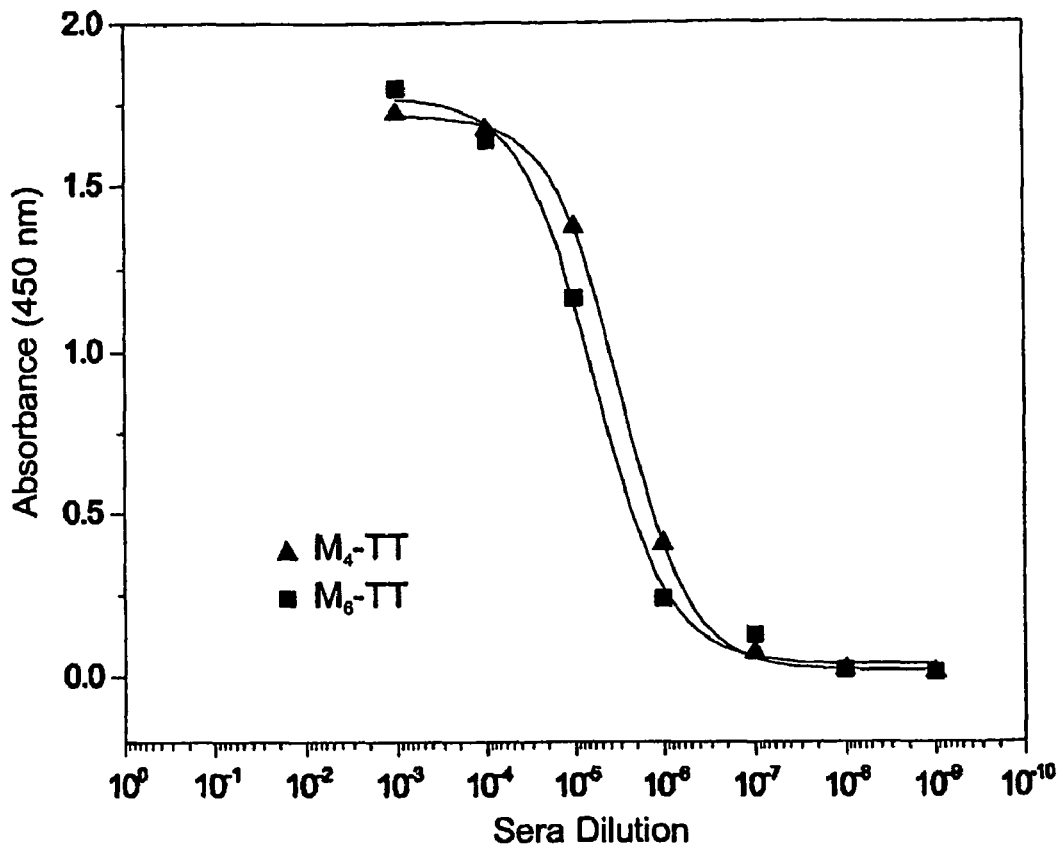
Titration of rabbit anti sera with *C. albicans* mannan antigen coated on ELISA plates. Antibodies were raised against (1→2)-β-D-mannotetrose ($M_4$-TT, 44) and (1→2)-β-D-mannohexaose ($M_6$-TT, 45) tetanus toxoid conjugates.

SYNTHETIC ANTI-*CANDIDA ALBICANS* OLIGOSACCHARIDE BASED VACCINES

BACKGROUND OF THE INVENTION

1. Field of the Invention

The present invention provides immunogenic oligosaccharide compositions and methods of making and using them. In particular, the compositions comprise native O-linked and S-linked oligosaccharides coupled to a protein carrier, wherein the resultant conjugate elicits a protectively immunogenic response, particularly in vaccines against pathogenic *Candida* species and more particularly against *Candida albicans*. Preferably the pathogenic *Candida* species are those that possess cell wall oligosaccharide compositions similar to the β-mannan component of *Candida albicans* cell walls.

REFERENCES

The following publications, patents and patent applications are cited in this application as superscript numbers.

1. Casadevall, A.; Cassone, A.; Bistoni, F.; Cutler, J. E.; Magliani, W.; Murphy, J. W.; Polonelli, L.; Romani, L. (1998) *Med. Mycol.* 36, Suppl. 1, 95-105.
2. Beck-Sagué, C. M.; Jarvis, W. R., (1993) *J. Infect. Dis.* 167, 1247-1251.
3. Landman, D.; Saurina, G.; Quale, J. M., (1998) *Clin. Infect. Dis.* 26:183-184.
4. Levitz, S. M., (1992) *Clin. Infect. Dis.,* 14(Suppl. 1), S3742.
5. Jouault, T.; Delaunoy, C.; Sendid, B.; Ajana, F.; and Poulain, D., (1997) *Clin. Diag. Lab. Immun.* 4, 328-333.
6. Shibata, N., Kobayashi, H., Tojo, M., & Suzuki, S. (1986) *Arch. Biochem. Biophys.* 251, 697-708.
7. Shibata, N.; Fukasawa, S.; Kobayashi, H.; Tojo, M.; Yonezu, T.; Ambo, A.; Ohkubo, Y.; Suzuki, S., (1989) *Carbohydr. Res.* 187, 239-253.
8. Han, Y.; Cutler, J. E., (1995) *Infect. Immun.* 63, 2714-2719.
9. Han, Y.; Cutler, J. E., (1997) *J. Infect. Dis.* 175, 1169-1175.
10. Han, Y., Riesselman, M. H.; Cutler, J. E., (2000) *Infect. Immun.* 68, 1649-1654.
11. Han, Y.; Kozel, T. R.; Zhang, M. X.; MacGill, R. S.; Carroll M. C.; Cutler. J. E., (2001) *J. Immunol* 167, 1550-1557.
12. Han, Y.; Kanbe, T.; Cherniak, R.; Cutler, J. E., (1997) *Infect. Immun.,* 65, 4100-4107.
13. Trinel, P-A.; Plancke, Y.; Gerold, P.; Jouault, T.; Delplace, F.; Shwarz, R. T.; Strecker, G.; Poulain, D., (1999) *J. Biol. Chem.* 274, 30520-30526.
14. Trinel, P. A.; Lepage, G.; Joulault, T.; Strecker, G.; Poulain, D., (1997) *FEBS Lett.,* 416, 203-206.
15. Han, Y.; Ulrich, M. A.; Cutler, J. E., (1999) *J. Infect. Dis.* 179, 1477-1484.
16. Gridley, J. J.; Osborn H. M. I., *J. Chem. Soc. Perkin Trans* 1, 2000, 1471-1491.
17. Barresi, F.; Hindsgual, O. Synthesis of β-D-mannose Containing Oligosaccharides. In Modern Methods in Carbohydrate Synthesis, Khan, S. H.; O'Neil, R. A. Eds; Harwood Academic Publishers: Amsterdam, 1996, 251-276.
18. Lergemüller, M.; Nukada, T.; Kuramochi, K.; Akhito, D.; Ogawa, T.; Ito, Y.; *Eur. J. Org. Chem.* 1999, 1367-1376.
19. Crich, D.; Sun, S.; *J. Am. Chem. Soc.* 1998, 120, 435436.
20. Nitz, M.; Purse, B. W.; Bundle, D. R., (2000) *Org. Lett.,* 2, 2939-2943.
21. Bundle, D. R.; Nitz, M., (2001) *J. Org. Chem.,* 66, 8411-8423.
22. Nitz, M.; Ling, C.-C.; Otter, A.; Cutler, J. E.; Bundle, D. R., (2002) *J. Biol. Chem.,* 277(5), 3440-3446.
23. Nitz, M. 2001. Ph.D. thesis. Synthesis of *Trichinella spiralis* and *Candida albicans* antigens, containing β-mannopyranosyl epitopes, their conformation and immunochemistry. University of Alberta, Edmonton, Alberta, May 4.
24. Cutler, J. E.; Han, Y., U.S. Pat. No. 5,578,309 Issued Nov. 26, 1996.
25. Bousquet, E.; Spadaro, A.; Pappalardo, M S.; Bernardini, R.; Romeo, R.; Panza, L.; Ronisvalle, G., (2000) *J. Carbohydr. Chem.* 19, 527-541.
26. Han, Y.; Morrison, R. P.; Cutler, J. E., (1998) *Infect. Immun.* 66, 5771-5776.
27. Kanbe, T.; Cutler, J. E., (1994) *Infect. Immun.,* 62, 1662-1668.
28. Kabat, E. A., (1962) *Federation Proc.* 21, 694-701.
29. Kabat, E. A., (1966) *J. Immunol.* 97, 1-11.
30. Rodriguez, E. C.; Marcaurelle, L. A.; Bertozzi, C. R., (1998) *J. Org. Chem.* 63, 7134-7135.

All of the above publications, patents and patent applications are herein incorporated by reference in their entirety to the same extent as if each individual publication, patent or patent application was specifically and individually indicated to be incorporated by reference in its entirety.

2. State of the Art

*Candida albicans*, the most common etiologic agent in candidiasis,[1] commonly affects immunocompromised patients and those undergoing long-term antibiotic treatment.[2] The number of cases of systemic candidiasis has become a major medical problem in hospitals.[2] Treatment of these infections is increasingly difficult due to drug resistance and the toxicity of known antifungal compounds.[3] Humoral and cell mediated immunity may both play a major role in host defenses against *C. albicans*. While most patients with serious mucosal infections have defects in their cellular immunity,[4] patients with deep tissue invasion seem to lack antibodies against the (12)-p-mannan oligomer found in the yeast cell wall.[5]

The β-mannan component of *Candida albicans* cell walls is a relatively small component of the much larger α-mannan to which it is attached via a phosphodiester group.[6,7] Not with standing the importance of the larger mannan in defining some *Candida* serogroups, the small β-mannan appears to hold potential as a protective antigen.

Monoclonal antibodies that protect mice against the pathogenic yeast, *C. albicans*[8,9,10] have been shown to be specific for the cell wall (1→2)-β-mannan antigen.[6,7] These antibodies raised against *C. albicans* cell wall extracts in mice were protective against disseminated candidiasis and vaginal candidiasis.[8-11] Further studies on these protective monoclonal antibodies indicated the active antigen to be a (1→2)-β-mannan polymer that is present as a component of the cell wall phopshomannan,[12] and separately as a phospholipomannan.[13] In both forms, the (1→2)-β-mannan antigen is relatively small consisting of between two to fourteen residues.[14] The immunochemistry and solution properties of this antigen are of great interest since (1→2)-β-mannan oligomers have potential as the key epitope of conjugate vaccines.[15]

The rational synthesis of β-mannosides is a longstanding problem in glycoside synthesis, that until recently, lacked a general solution despite several novel approaches.[16-19] In the construction of large homo-oligomers, the separation of anomeric mixtures posed a major obstacle to efficient assembly by either block or sequential chain extension reactions.

The synthesis of these unique polymers required modifications of existing procedures for the synthesis of β-D-mannopyranosides. The modulation of the glycosyl donor's reactivity, by the introduction of p-chlorobenzyl protecting groups, was required to stabilize the ulosyl bromide to the innovative reaction conditions. These conditions employed a sterically hindered participating solvent and a soluble promoter to control the stereochemistry of the glycosylation, providing synthetic access to the interesting (1→2)-β-D-mannopyranans.[20-23] Preparation of these compounds has facilitated further studies into the interesting structural properties and activity of the (1→2)-β-D-mannopyranosides and provided a three dimensional solution structure that accounts for the immunochemical properties of this antigen.[22]

SUMMARY OF THE INVENTION

In one aspect, this invention provides for conjugates comprising an oligosaccharide comprising (1→2)-β-D-mannopyranose or a (1→2)-β-D-mannopyranose derivative, wherein each saccharide unit of said oligosaccharide is linked via an inter-glycosidic atom selected from the group consisting of oxygen and sulfur, a protein carrier, and a linking group, wherein the oligosaccharide and the protein carrier are covalently conjugated to one another through the linking group. In addition the conjugate produces an immune response in a mammal against *Candida* species, wherein this response possesses immunological memory. In a preferred embodiment the *Candida* species is *Candida albicans*.

In a preferred embodiment the conjugate is an oligosaccharide selected from the group consisting of disaccharides through hexasaccharides of (1→2)-β-D-mannopyranose or (1→2)-β-D-mannopyranose derivatives. In a further preferred embodiment, the oligosaccharide is the trisaccharide β-D-mannopyranose-(1→2)-βD-mannopyranose-(1→2)-β-D-mannopyranose or the disaccharide β-D-mannopyranose-(1→2)-β-D-mannopyranose.

In another preferred embodiment, the inter-glycosidic atom is sulfur. Preferably an inter-glycosidic atom at a terminal non-reducing end of the oligosaccharide is sulphur, a form that is expected to be more resistant to hydrolysis by mammalian enzymes and hence a more persistent antigen, yielding superior immune responses.[21,23,25]

In yet another preferred embodiment the linking group is derived from heterobifunctional or homobifunctional cross coupling reagents, preferably, diethyl squarate, di-$NH_2$ or di-$CO_2H$ capped polyoxyalkylenes (such as Jeffamines), succinic anhydride, or maleic anhydride. Alternatively the linking group is derived from a mammalian lipid mimic or a bacterial lipid mimic wherein the mammalian lipid mimic or a bacterial lipid mimic is functionalized to permit covalent attachment to a protein or peptide carrier. Preferably the mammalian lipid mimic or a bacterial lipid mimic is selected from the group consisting of sphingosine, a diacyl glycerol, and a diphytanyl ether of glycerol, {2,3-di-O-[(3R, 7R, 11R)-3,7,11,15-tetramethylhexadecanyl]-sn-glycerol}.

In yet another preferred embodiment the protein carrier is selected from the group consisting of bovine serum albumin, (BSA), human serum albumin, (HSA), tetanus toxoid, (TT) a recombinant outer membrane class 3 porin (rPorB) from group B *Neisseria meningitidis*, and peptide carriers such as PADRE. In one embodiment, the protein carrier is tetanus toxoid or bovine serum albumin.

In another aspect, this invention drawn to an anti-*Candida* species vaccine comprising the conjugate as described above and a pharmaceutically acceptable adjuvant. In a preferred embodiment the *Candida* species is *Candida albicans*.

In yet another aspect, this invention is drawn to a method of preventing or ameliorating infection by a *Candida* species which method comprises administering to a mammal an immunogenic effective amount of an anti-*Candida* species vaccine comprising a conjugate as described above and a pharmaceutically acceptable adjuvant. In a preferred embodiment the *Candida* species is *Candida albicans*. In a particularly preferred embodiment the vaccine is directly administered to the urogenital track and more preferably with a topical composition.

BRIEF DESCRIPTION OF THE DRAWINGS

This invention will be further described with reference being made to the accompanying drawings.

FIG. 7 illustrates the inhibition of the binding of lgM monoclonal antibody B6.1 to *C. aibicans* mannan extract by propyl mannosides (17, 18, 19, 32, 21).

FIG. 9 illustrates titration of rabbit anti sera with *C. albiccins* mannan antigen coated on ELISA plates. Antibodies were raised against (1→2)-β-D-mannotetraose ($M_4$-TT, 44) and (1→2)-β-D-mannohexaose ($M_6$-TT, 45) tetanus toxoid conjugates.

DETAILED DESCRIPTION OF THE INVENTION

The present invention provides immunogenic oligosaccharide compositions and methods of making and using them. In particular, the compositions comprise oligosaccharides coupled to a carrier protein, wherein the resultant conjugate elicits a protectively immunogenic response, particularly in vaccines against pathogenic *Candida* species. In addition and of especial note is the use of S-linked oligosaccharide as an especially effective hapten for use in conjugate vaccines where such groups secure an enhanced immune response toward carbohydrate epitopes. However, prior to describing this invention in further detail, the following terms will first be defined:

Definitions

The term "oligosaccharide" refers to a carbohydrate structure having from 2 to about 14 saccharide units wherein each of the saccharide units is linked via an inter-glycosidic atom selected from the group consisting of oxygen and sulfur.

The particular saccharide units employed are not critical and include, by way of example, all natural and synthetic derivatives of D-mannose, glucose, galactose, N-acetylglucosamine, N-acetyl-galactosamine, fucose, sialic acid, 3-deoxy-D,L-octulosonic acid, and the like.

In addition to being in their pyranose form, all saccharide units described herein are in their D form except for fucose, which is in its L form.

The term "mannopyranose" refers to a 6-carbon (hexose) sugar having a six-membered ring containing five carbon atoms and one oxygen atom and of formula (I):

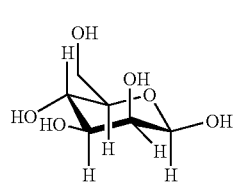

(I)

The term "mannopyranose derivatives" refers to mannopyranose as described above with at least one hydrogen of the ring hydroxyl groups is replaced by another chemical moiety, preferably an acetyl or $C_2$-$C_6$ acyl group or a protecting group such as a benzyl or a p-chlorobenzyl group. The acetyl and acyl derivatives are preferably hydrolyzed in vivo to form a mannopyranose conjugate. The protecting groups, on the other hand, are preferably removed prior to administration.

Figure 1:
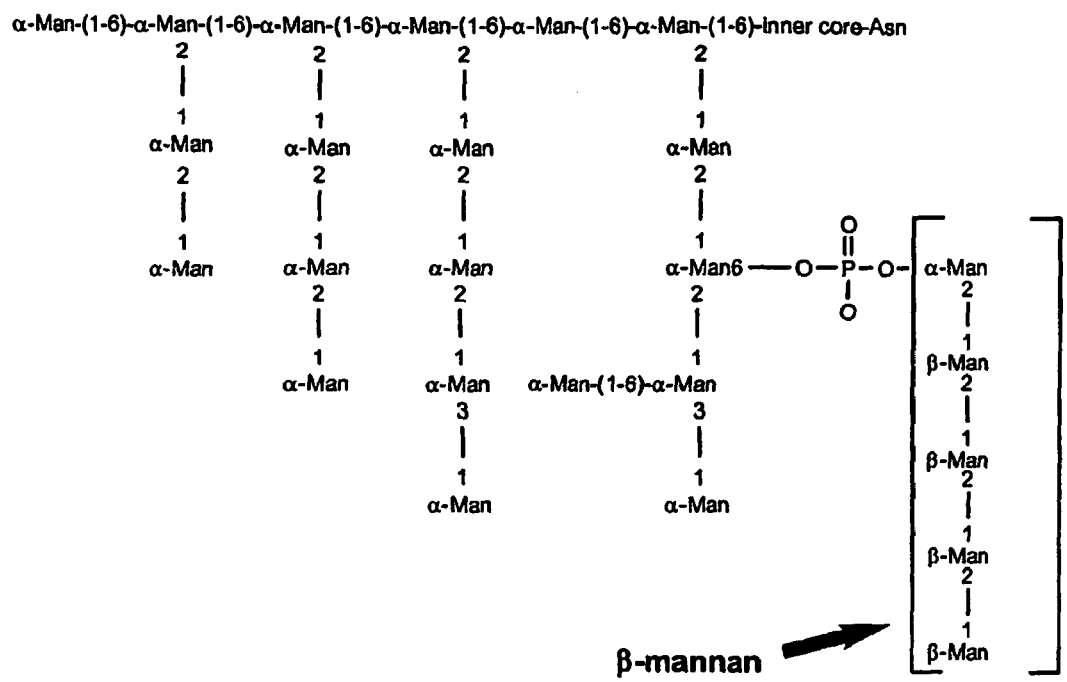
FIG. 1 illustrates the structure of a portion of *Canida albicans* N-linked mannan, wherein the glycan chain lengths vary.

The term "mannan" with respect to *Candida* and yeasts in general refer to a complex polymannose polymer that is N-linked via asparagines to a protein. The structure is shown FIG. 1.

The polysaccharide is exclusively mannose containing and very complex with branching side chains. For the most part the main chain and branches are all alpha linked mannopyranose residues, however in most *Candida* there is a short chain linked via a phosphate ester to the main alpha linked mannan. This short chain varies in length from 2 beta linked mannopyranose residues up to 10-14 mannopyranose residues.

The term mannan is most often used to mean the whole complex. When part of the complex is being referred to it could be called alpha mannan (also called acid stable mannan) or beta mannan. The later is also called the acid labile mannan because it is easily cleaved off.

The term "protein carrier" or "carrier" refers to a substance that elicits a thymus dependent immune response that can be coupled to a hapten or antigen to form a conjugate. In particular, various protein and/or glycoprotein and/or sub-unit carriers can be used, including but not limited to, tetanus toxoid/toxin, diphtheria toxoid/toxin, bacteria outer membrane proteins, crystalline bacterial cell surface layers, serum albumin, gamma globulin or keyhole limpet hemocyanin.

The term "conjugate" refers to oligosaccharides that have been covalently coupled to a protein or other larger molecule with a known biological activity through a linker. The oligosaccharide may be conjugated through the inter-glycosidic oxygen or sulfur.

The oligosaccharide is attached though a linker to a protein carrier using conventional chemical techniques providing for linkage of the oligosaccharide to the carrier. In one embodiment, reaction chemistries well known in the art that result in covalent linkages between the linker and both the protein carrier and the oligosaccharide and are used. Such chemistries preferably involve the use of complementary functional groups on the hetero- or homo-bifunctional cross-coupling reagent. Preferably, the complementary functional groups are selected relative to the functional groups available on the oligosaccharide or protein carrier for bonding or which can be introduced onto the oligosaccharide or carrier for bonding. Again, such complementary functional groups are well known in the art. For example, reaction between a carboxylic acid of either the linker or the protein and a primary or secondary amine of the protein or the linker in the presence of suitable, well-known activating agents results in formation of an amide bond; reaction between an amine group of either the linker or the protein and a sulfonyl halide of the protein or the linker results in formation of a sulfonamide bond covalently; and reaction between an alcohol or phenol group of either the linker or the protein carrier and an alkyl or aryl halide of the carrier or the linker results in formation of an ether bond covalently linking the carrier to the linker. Similarly these complimentary reactions can occur between the linker and the oligosaccharide to form a linkage between the oligosaccharide and the linker. The table below illustrates numerous complementary reactive groups and the resulting bonds formed by reaction there between.

Complementary Binding Chemistries

| FIRST REACTIVE GROUP | SECOND REACTIVE GROUP | LINKAGE |
|---|---|---|
| hydroxyl | isocyanate | urethane |
| amine | epoxide | β-hydroxyamine |
| amine | ketone | imine |
| amine | ketone | secondary amine |
| sulfonyl halide | amine | sulfonamide |
| carboxyl | amine | amide |
| acyl azide | amine | amide |
| hydroxyl | alkyl/aryl halide | ether |
| epoxide | alcohol | β-hydroxyether |
| epoxide | sulfhydryl | β-hydroxythioether |
| maleimide | sulfhydryl | thioether |
| carbonate | amine | carbamate |

The term "heterobifunctional cross coupling reagents" refers to a reagent that is used to couple two other molecules or species together by having two different functional groups built into one reagent. Such cross coupling reagents are well known in the art and include, for example, X-Q-Xβ, where each of X and X' are preferably independently cross coupling groups selected, for example, from —OH, —$CO_2$H, epoxide, —SH, —N=C=S, and the like. Preferably Q is a group covalently coupling X and X' having from 1 to 20 atoms and preferably from 1 to 20 carbon atoms. Examples of suitable heterobifunctional cross coupling reagents include squarate derivatives, as found in the attached appendix, as well as entities derived from succinic anhydride, maleic anhydride, polyoxyalkylenes, adepic acid ($CO_2$H—$C_6$—$CO_2$H) and azelaic acid ($CO_2$H—$C_9$—$CO_2$H). The heterobifunctional cross coupling reagents may also be a lipid or lipid mimic, where the carbohydrate hapten may be covalently linked to the lipid or the lipid is co-administered as an immunological adjuvant.

The term "homobifunctional cross coupling reagents" refers to a reagent that is used to couple two other molecules or species together by having two of the same functional groups built into one reagent. Such cross coupling reagents are well known in the art and include, for example, X-Q-X, where X and Q are as defined above. 1,2-Diaminoethane, a dicarboxylic acid chloride and diethyl squarate are examples of such homobifunctional cross coupling reagents. Homobifunctional cross coupling reagents may also be derived from lipids and lipid mimics.

The term "linker" or "linking group" refers to the residue produced after covalent bonding of the homobifunctional or heterobifunctional cross coupling reagent to the oligosaccharide and the protein carrier.

The term "vaccine" refers to a composition used to stimulate an immune response in a mammal and so confer resistance to the disease or infection in that mammal, which used herein, infers that the response has immunologic memory.

The term "adjuvant" refers to a nonantigenic substance (such as aluminium hydroxide) that, in combination with an antigen, enhances antibody production by inducing an inflammatory response, which leads to a local influx of antibody-forming cells. Adjuvants are used therapeutically in the preparation of vaccines, since they increase the production of antibodies against small quantities of antigen and lengthen the period of antibody production.

The term "immune response" refers to the reaction of the body to foreign or potentially dangerous substances (antigens), particularly disease-producing microorganisms. The response involves the production by specialized white blood cells (lymphocytes) of proteins known as antibodies, which react with the antigens to render them harmless. The antibody-antigen reaction is highly specific. Vaccines also stimulate immune responses.

The term "immunologic memory" refers to the ability of the immune system to remember a previously encountered antigen. Antibodies are produced as a result of the first exposure to an antigen and stored in the event of subsequent exposure.

The term "immunologically effective amount" refers to the quantity of a immune response inducing substance required to induce the necessary immunological memory required for an effective vaccine.

Utility, Formulations and Testing

The present oligosaccharide-protein conjugates of the β-mannan component of *Candida albicans* cell wall antigen are useful in vaccines against any *Candida* species possessing the β-mannan antigen, particularly *C. albicans*.

The conjugates of this invention may be used as vaccines, as immunogens that elicit specific antibody production or stimulate specific cell mediated immunity responses. They may also be utilized as therapeutic modalities, for example, to stimulate the immune system to recognize tumor-associated antigens; as immunomodulators, for example, to stimulate lymphokine/cytokine production by activating specific cell receptors; as prophylactic agents, for example, to block receptors on cell membrane preventing cell adhesion; as diagnostic agents, for example, to identify specific cells; and as development and/or research tools, for example, to stimulate cells for monoclonal antibody production Pharmaceutical Compositions The pharmaceutical compositions of the present invention are advantageously administered in the form of injectable compositions. A typical composition for such purpose comprises a pharmaceutically acceptable carrier. For instance, the composition may contain human serum albumin in a phosphate buffer containing NaCl. Other pharmaceutically acceptable carriers include aqueous solutions, non-toxic excipients, including salts, preservatives, buffers and the like (REMINGTON'S PHARMACEUTICAL SCIENCES, 15th Ed., Easton ed., Mack Publishing Co., pp 1405-1412 and 1461-1487 (1975) and THE NATIONAL FORMULARY XIV, 14th Ed., American Pharmaceutical Association, Washington, D.C. (1975), both hereby incorporated by reference). Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. The pH and exact concentration of the various components the pharmaceutical composition are adjusted according to routine skills in the art. Goodman and Gilman, THE PHARMACOLOGICAL BASIS FOR THERAPEUTICS (7th ed.).

Typically, such vaccines are prepared as injectables, either as liquid solutions or suspensions; solid forms suitable for solution in, or suspension in, liquid prior to injection may also be prepared. The preparation also may be emulsified. The active immunogenic ingredient is often mixed with an excipient that is pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH-buffering agents, adjuvants or immunopotentiators that enhance the effectiveness of the vaccine.

Adjuvants may increase immunoprotective antibody titers or cell mediated immunity response. Such adjuvants could include, but are not limited to, Freunds complete adjuvant, Freunds incomplete adjuvant, aluminium hydroxide, dimethyldioctadecylammonium bromide, Adjuvax (Alpha-Beta Technology), Inject Alum (Pierce), Monophosphoryl Lipid A (Ribi Immunochem Research), MPL+TDM (Ribi Immunochem Research), Titermax (CytRx), toxins, toxoids, glycoproteins, lipids, glycolipids, bacterial cell walls, subunits (bacterial or viral), carbohydrate moieties (mono-, di-, tri- tetra-, oligo- and polysaccharide) various liposome formulations or saponins. Combinations of various adjuvants may be used with the conjugate to prepare the immunogen formulation.

In another embodiment, the conjugate is formulated for topical applications including gels, lotions, creams and the like. Topical formulations are well known in the art.

A topical formulation may be prepared as follows:

| Ingredient | Quantity |
| --- | --- |
| Active Ingredient | 1-10 g |
| Emulsifying Wax | 30 g |
| Liquid Paraffin | 20 g |
| White Soft Paraffin | 20 to 100 g |

The white soft paraffin is heated until molten. The liquid paraffin and emulsifying wax are incorporated and stirred until dissolved. The active ingredient is added and stirring is continued until dispersed. The mixture is then cooled until solid.

The vaccines are conventionally administered intraperitoneally, intramuscularly, intradermally, subcutaneously, orally, nasally, parenterally or administered directly to the urogenital tract, preferably topically, to stimulate mucosal immunity. Additional formulations are suitable for other modes of administration and include oral formulations. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders and contain 10%-95% of active ingredient, preferably 25-70%.

The term "unit dose" refers to physically discrete units suitable for use in humans, each unit containing a predetermined quantity of active material calculated to produce the desired therapeutic effect in association with the required diluent, i.e., carrier or vehicle, and a particular treatment regimen. The quantity to be administered, both according to number of treatments and amount, depends on the subject to be treated, capacity of the subject's immune system to synthesize antibodies, and degree of protection desired. The precise amounts of active ingredient required to be administered depend on the judgment of the practitioner and are peculiar to each individual. However, suitable dosage ranges are on the order of one to several hundred micrograms of active ingredient per individual. Suitable regimes for initial administration and booster shots also vary but are typified by an initial administration followed in one or two week intervals by one or more subsequent injections or other administration. Annual boosters may be used for continued protection.

Methods and Procedures

The methods and procedures suitable for preparing the compositions and vaccines of this invention are found in references 20-23.

Synthesis of (1→2)-β-mannopyranosyl oligomers.

Synthesis of β1,2 linked oligomers of mannose have been realized for the first time[20] by an iterative synthetic procedure, whereby a suitable glycosyl donor in this case ulosyl bromide 1 or its related derivative 2 react with selectively protected mono through pentasaccharide alcohols 3-7 to provide first the corresponding ulopyranoside (e.g. oliosaccharide bearing a terminal residue with the 2-keto function), which is reduced to afford directly a selectively protected oligosaccharide alcohol (e.g. 4-7) to be used in subsequent chain elongation steps (FIG. 2).[20,21] The donors 1 and 2 are attractive because of their high diastereoselectivity over the glycosylation and reduction steps, and the minimization of the number of protecting groups required. The p-chlorobenzyl protected ulosyl bromide 2 is the preferred glycosyl donor.

Figure 2:
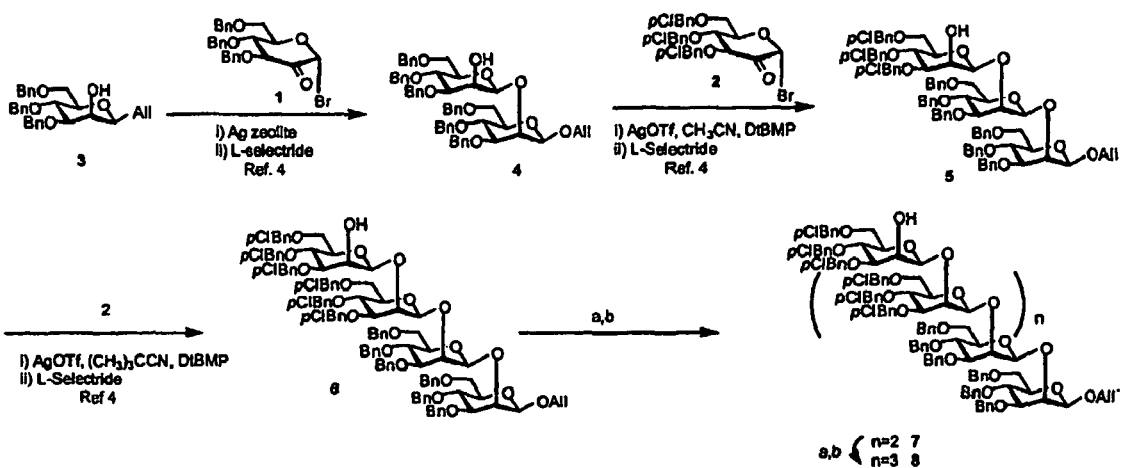
FIG. 2 illustrates a synthesis of di through hexasaceharide (1→2)-β-D-mannopyranan oligomers ((a) 2, AgOTf, DtBMP, $(CH_3)_3CCN/CH_2Cl_2$; (b) L-Selectride, THF).

The synthesis of disaccharide through hexasaccharides was accomplished as outlined in FIG. 2 with pivaloyl nitrile as a participating solvent to promote formation of equatorial glycosides. The steric bulk of the t-butyl group decreases side reactions at the nitrile carbon. This combination of a participating solvent and soluble promoters are superior to the heterogeneous conditions initially employed for the glycosylation of the complex alcohols.[20] Pentasaccharide (7) and hexasaccharide (8) were synthesized employing these conditions in 51% and 48% yield respectively (combined yield of glycosylation and reduction steps).[21] p-Chlorobenzyl protected ulosyl bromide 2 was found to give higher glycosylation yields than its benzyl protected counterpart 1 due to the increased stability of the protecting groups. Formation of the ulosides was accomplished with good stereoselectivity giving an approximate 4:1 β:α mixture. Separation of the undesired α-anomer was readily accomplished by silica gel chromatography of the protected oligomer after reduction of the product obtained from the glycosylation. Excellent diastereoselectivity was observed upon reduction of the β ulopyranoside to the desired β-mannoside with L-selectride, since no β-gluco epimer could be detected by $^1$H NMR in this reaction. Heteronuclear one bond coupling constants were used to unambiguously establish the anomeric configuration of the β-mannopyransyl residues.[21]

The yields and selectivity achieved in this synthesis compare well with those reported using 4,6-O-benzylidene protected mannopyranosyl sulphoxide donors.[19] Crich et al. synthesized β-(1→2) mannopyranosyl pentasaccharides and hexasaccharides in 68% and 69% respectively but their method requires an extra deprotection step (achieved in 80-85% yield) prior to further glycosylation steps, and no large gain in efficiency is evident (cf reference 19 vs 21).

Figure 3:
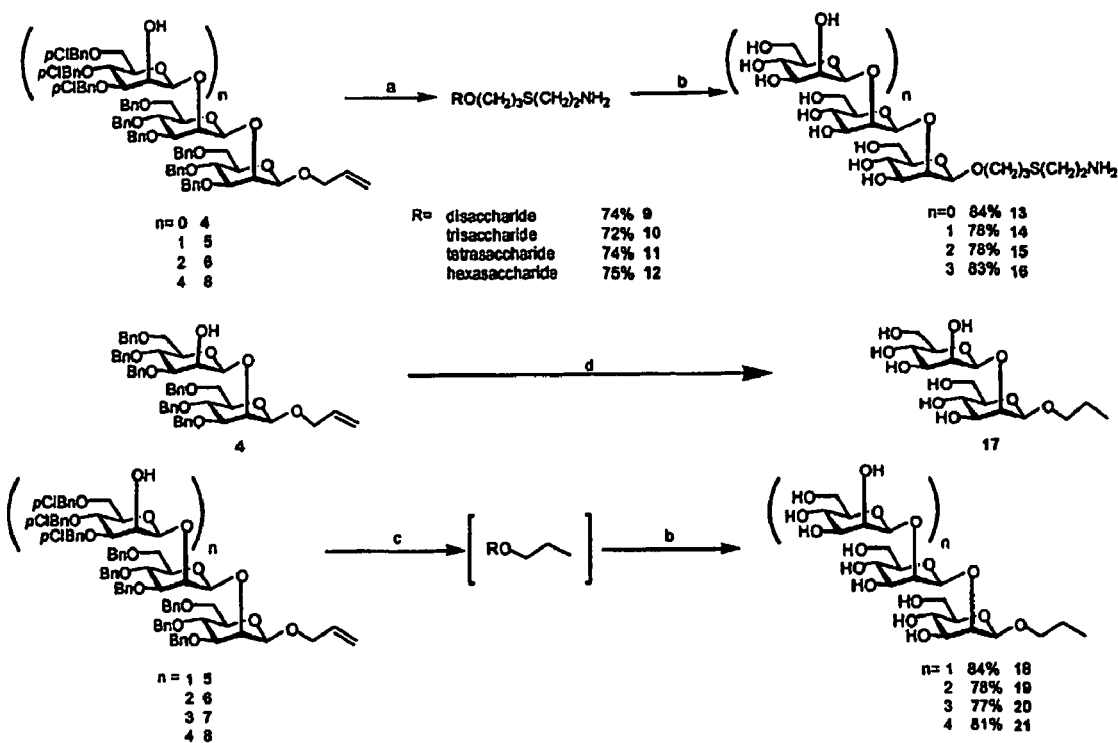
FIG. 3 illustrates a process of deprotection of (1→2)-β-D-mannopyranan oligomers ((a) 2-aminoethanethiol hydrochloride, MeOH/$CH_2Cl_2$, hv 365 nm; (b) Na/$NH_3$, tBuOH, THF; (c) $NH_2NH_2.H_2O$, EtOH/THF; (d) Pd/C, $H_2$, EtOH).

The protected oligosaccharides (4-6 and 8) were elaborated via photo addition of 2-aminoethanethiol to the allyl glycosides to give the amine functionalized glycosides (9-12).[21] It was necessary to use long wave (365 nm) UV irradiation to avoid complications with the aromatic protecting groups (FIG. 3). Purification of these compounds was difficult, and they were carried through the subsequent deprotection step with minor impurities. Compounds (9-12) were deprotected under dissolving metal conditions to yield the amino functionalized glycosides (13-16) after purification. Deprotection of compounds (4-8) to their respective propyl glycosides (17-21) was most efficiently achieved using a two step procedure. The allyl glycoside was first reduced to the propyl glycoside via diimide reduction and then the protecting groups were removed under dissolving metal conditions (FIG. 3).

Synthesis of Thioglycoside Mimetic

Figure 4:
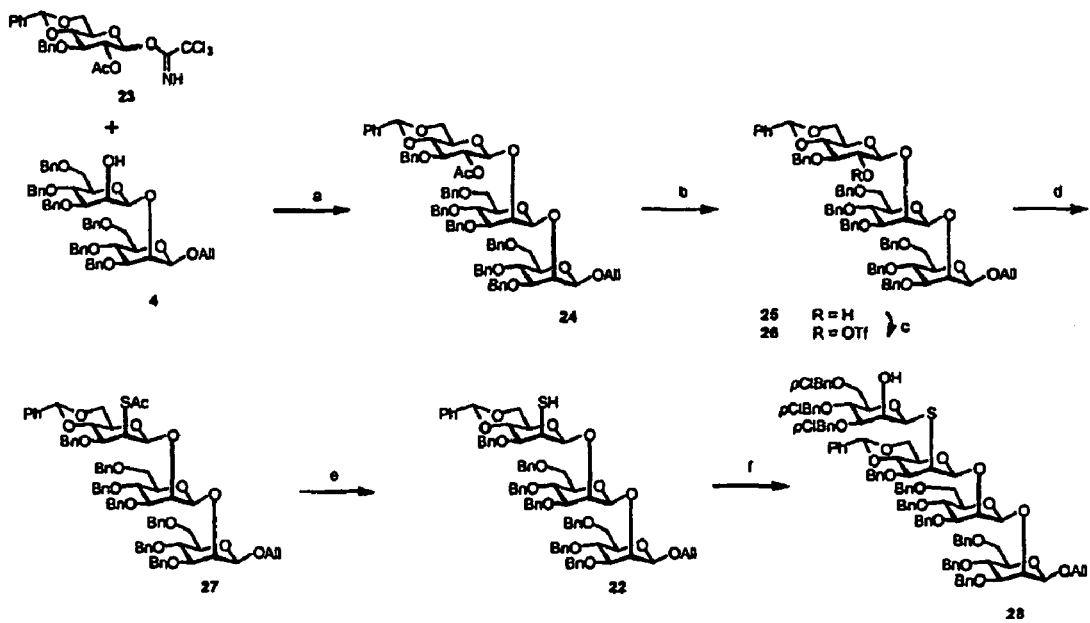
FIG. 4 illustrates a synthesis of the thioglyoside mimetic of(1→2)-β-D-mannopyranoletraose ((a) TMSOTf, $CH_2Cl_2$, 76%; (b) MeONa, MeOH/THF, 94%; (c) $Tf_2O$, pyridine. 89%; (d) KSAc, DMF, 63%; (e) hydrazine hydrate, cyclohexene, EtOH/THF, 89%; (f) i. 2, lutidine, $CH_2Cl_2$, ii. L-Selectride, THF, 49%).
Figure 5:
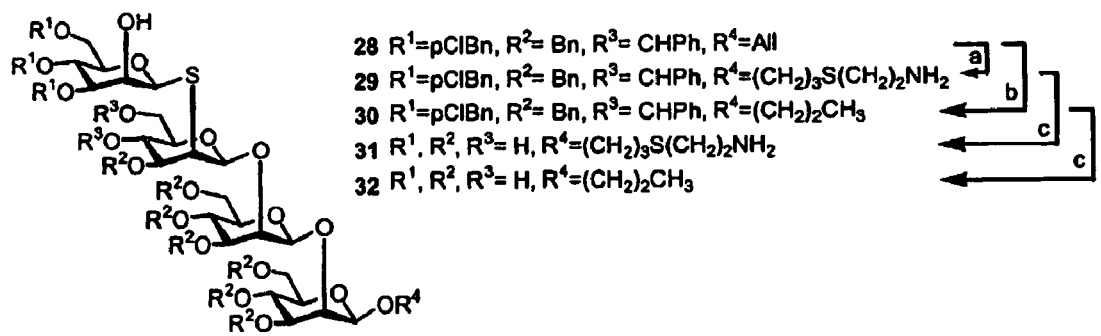
FIG. 5 illustrates a process of deprotection of the thioglyoside mimetic of(1→2)-β-D-mannopyranotetraose ((a) 2-aminoethanethiol hydrochloride, MeOH/$CH_2Cl_2$, hv 365 nm; (b) $NH_2NH_2.H_2O$, EtOH/THF; (c) Na/$NH_3$, tBuOH, THF).

Installation of a terminal thioglycosidic linkage was accomplished by reaction of a trisaccharide thiol 22 with the ulosyl bromide 2 (FIG. 4). Trisaccharide, 22, was synthesized by glycosylation of disaccharide 4, with the glucosyl donor 23, to give trisaccharide 24. The trichloracetimidate donor 23 was prepared from 3-O-benzyl glucose according to standard conditions.[21] Trisaccharide 24 was obtained in high yield from the imidate donor 23 and the disaccharide acceptor 4. Transesterification of trisaccharide 24 gave alcohol 25, which was converted to the 2-O-trifluoromethanesulfonate 26 under standard conditions. Nucleophilic displacement of the triflate with thioacetate gave 27 and removal of the acetate proceeded smoothly to the thiol 22. Reaction of 22 with 2 under basic conditions gave, after reduction, tetrasaccharide, 28, in 49% yield. The corresponding 1-thio-α-gluco epimer was also isolated from the reaction (~12%). The tetrasaccharide 28 was converted to the corresponding 3-(2-aminoethylthio)-propyl glycoside 29 as described for compounds 9-12. The tetrasaccharide 28 was reduced with a solution of hydrazine hydrate, to afford the propyl glycoside 30. Dissolving metal conditions then efficiently removed the benzyl and p-chlorobenzyl protecting groups of compounds 29 and 30 to give the desired tetrasaccharides, 31 and 32 (FIG. 5).

Formation of Glycoside Conjugates.

Figure 6:
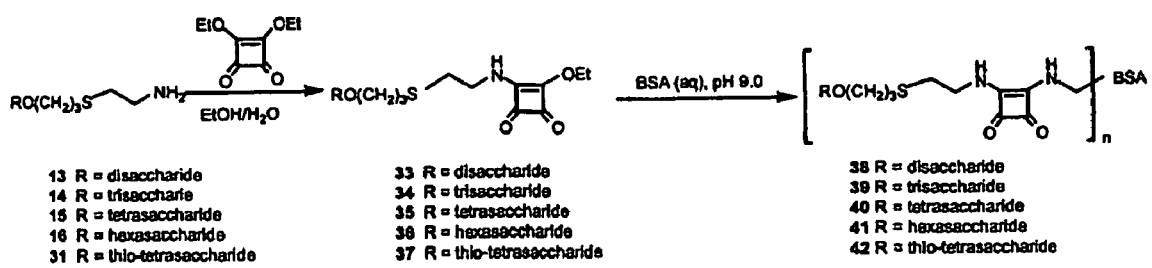
FIG. 6 illustrates a synthesis of the oligomannoside squarate conjugates.

Reaction of the functionalized mannopyranosyl glycosides 13-16 and 31 with diethyl squarate in a solution of ethanol and water provided, in high yield, the activated oligosaccharides 33-37 (FIG. 6). Coupling to BSA and tetanus toxoid was performed as follows: either BSA or tetanus toxoid (~20 mg/ml) was dissolved in borate buffer ($Na_2BO_4$ 0.07M, $KHCO_3$ 0.035M, pH 9.5) the squarate coupled carbohydrate was then added and the reaction was left for 72 h at room temperature. The reaction was then diluted with deionized water and dialysed in a MICROSEP microconcentrator against 5 changes of deionized water (3 ml) where the final volume after concentration was no greater than 500 μL. The solution from the final concentration was lyphophilized to a white solid. MALDI mass spectrometry was preformed on a Voyager elite system from Applied Biosystems. Conjugation efficiencies of between 65-70% were achieved with an incorporation of 13-15 ligands for a 20 fold molar excess of activated oligosaccharide. Targeted and observed incorporations are tabulated below (Table 1). The molecular weights of the protein conjugates determined by MALDI-TOF spectroscopy indicated that all the conjugates had a degree of hapten incorporation within a narrow range of ±1 haptens.

TABLE 1

Protein carbohydrate conjugates

| Oligosaccharide | Target incorporation (100% conversion) | Incorporation achieved | Incorporation efficiency |
|---|---|---|---|
| 38 $M_2$-BSA | 20 | 16 | 80 |
| 39 $M_3$-BSA | 20 | 15 | 75 |
| 40 $M_4$-BSA | 20 | 13 | 65 |
| 41 $M_6$-BSA | 20 | 10 | 50 |
| 42 $SM_4$-BSA | 20 | 15 | 75 |
| 43 $SM_4$-TT | 80 | 33 | 41 |
| 44 $M_4$-TT | 80 | 27 | 34 |
| 45 $M_6$-TT | 80 | 29 | 36 |

$M_3$ (1→2)-β-D-mannopyranotriose, $M_4$ (1→2)-β-D-mannopyranotetrose, $SM_4$ (1→2)(1-thio-β-D-mannopyranosyl)(1→2)-β-D-mannopyranotriose, $M_6$ (1-2)-β-D-mannopyranohexose Preferably the conjugates of the present invention exclude conjugates that originate from the use of a reducing sugar residue to make the linkage to the protein carrier either directly or via a tether using reactions such as the conversion of a terminal alditol to an aldehyde and hence coupling by reductive amination to an amine or lysine, its conversion to a carboxylic acid derivative or the direct coupling of a terminal aldose by reductive amination or by creation of a glycosylamine and then coupling via its amino group.

Binding of propyl (1→2)-β-mannosides to Monoclonal Antibodies

Two antibodies produced in response to a C. albicans native antigen liposomal vaccine[15] and which protect mice against live challenge with C. albicans[10,26] were used to evaluate the biological activity of the synthetic oligomanns 17-21 and 32. These monoclonal antibodies are IgM B6.1 and IgG C3.1. The affinity of these monoclonal antibodies for the synthesized propyl glycosides was determined in a competitive inhibition ELISA. The monoclonal antibodies, MAb B6.1 (IgM) and MAb C3.1 (IgG3) were produced as concentrated tissue culture supernatants and diluted ~1:40,000 (B6.1) and ~1:2000 (C3.1). C. albicans mannan obtained by 2-mercaptoethanol extraction of whole cells without subsequent affinity fractionation[27] was dissolved in PBS (10 μg/mL) and the solution was used to coat 96 well ELISA plates (100 μL, 18 h at 4° C.). The plate was washed five times with PBST containing Tween 20, 0.05% v/v) and blocked for 1 h at room temperature (2% BSA PBS, 100 μL). The monoclonal antibodies were mixed with inhibitor dissolved in PBST at concentrations in the range between 0.1 μM to 1 mM, and the resulting solutions were added to the coated microtitre plate in triplicate and incubated at room temperature for 18 h. The plate was washed with PBST (5×), and goat anti-mouse (IgG or IgM) antibody conjugated to horseradish peroxidase (diluted 1:2000, Kirkegaard and Perry Lab) in PBST (100 μL) was added and incubated for 1 h at room temperature. The plate was washed with PBST (5×), 3,3',5,5'-tetramethylbenzidine (TMB, 100 μL, Kirkegaard and Perry Lab) was added, and after 2 minutes the colour reaction was stopped by the addition of 1M phosphoric acid (100 μL). Absorbance was read at 450 nm and percent inhibition was calculated relative to wells containing antibody without inhibitor, and the concentration of ligand that gives 50% inhibition is quoted as an $IC_{50}$ value.

The IgM antibody B6.1 shows a surprisingly high affinity for the di and trisaccharides when compared to the tetra and hexasaccharides. The propyl (1-thio-β-D-mannopyranosyl)-(1→2)-β-D-mannopyranotrioside falls between the tri and tetrasaccharide in affinity (FIG. 7).

Figure 8:
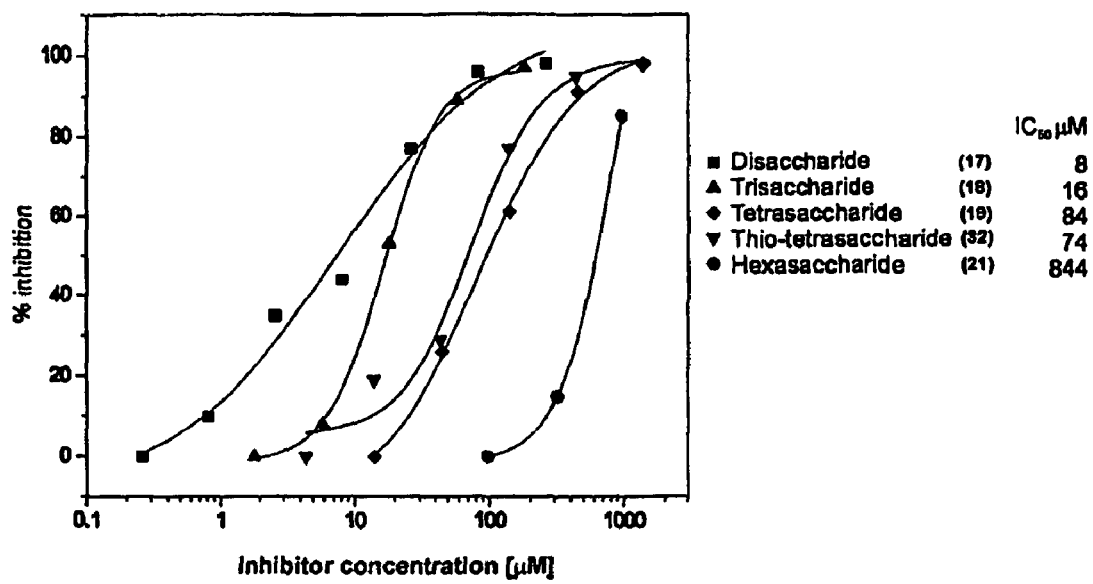
FIG. 8 illustrates the inhibition of the binding of lgG monoclonal antibody to *C. albicans* mannan extract with propyl mannosides (17, 18, 19, 32, 21). The origin of the flattened binding curve for the disaccharide is unknown.

The IgG antibody showed a similar trend of affinities, to that of the IgM antibody, for the same panel of oligo-mannans. Di- and trisaccharides had higher affinities, five and two fold respectively, for the IgG antibody than for the IgM MAb and the remaining antigens had a similar affinity (FIG. 8). The observation of higher affinity for smaller oligomers is unprecedented for antibodies generated to polysaccharide antigens. As a rule the larger oligomers have higher affinity for the antibodies.[28,29] The expected trend is to observe oligomer inhibition that increases with oligosaccharide length to a maxium of 5-8 hexose residues.[28,29]

Furthermore, it is very surprising that the IgG and IgM antibodies have similar specificity and affinity. A polydisperse antigen such as the extract used to generate antibodies B6.1 and C3.1[15] would be expected to generate antibodies to differing epitopes. The finding that both monoclonal antibodies recognize similar epitopes suggests a single immunodominant epitope in the extract of the C. albicans cell wall used for immunization. As these antibodies are known to be protective, the inhibition results indicate a near ideal situation for the generation of synthetic vaccines.[22] This unexpected result has been rationalized with the compact helical nature of the (1→2)-β-mannan polymer and potential steric interactions with the binding site. This finding suggests a synthetically simple disaccharide or trisaccharide conjugate may be all that is necessary to generate a protective immune response.

Immunization of Experimental Rabbits with Tetrasaccharide-TT Conjugate 44 and Hexasaccharide-TT Conjugate 45

2 New Zealand white rabbits where immunized with a tetanus toxoid protein conjugate (50 μg in 500 μL PBS and 500 μL Freunds complete adjuvant, homogenised) in three injections one intramuscularly in the rear thigh and two subcutaneously. On day 36 the rabbits were boosted with (50 μg in 500 μL PBS and 500 μL Freunds incomplete adjuvant, homogenised). On day 59 a third boost with (50 μg in 500 μL PBS and 500 μL Freunds incomplete adjuvant, homogenised) was carried out and on day 70 the rabbits were sacrificed. The titers of antibodies produced in rabbits were analyzed by ELISA.

96 well ELISA plates were coated with β-mannan preparation extracted from Candida albicans and the plate was washed. Serial dilutions of the sera from the immunized animal were added to the plate in triplicate. Goat anti-rabbit horse radish peroxidase conjugated antibody was used to quantify specific antibody.[23]

Rabbits immunized with the tetanus toxoid conjugates exhibited a strong IgG response after three injections. A high titers were observed for the immunizing antigen and in addition these antibodies showed extremely strong specificity for C. albicans native antigen with a titre between $10^5$-$10^6$ (FIG. 9). Both the hexa and tetrasaccharide TT conjugates raised similar antibody titers.

Antibody Levels in Mice

Mice developed a strong IgM response against the hexasaccharide tetanus toxoid conjugate after two immunizations, as judged by ELISA assay, using the BSA conjugated hexasaccharide. Modest IgG antibodies were also present after this time. Groups of 5 mice were given monthly injections of 5-10 ug of the $SM_4$-TT conjugate. Two mice were sacrificed after the sixth injection and using standard hybridoma protocols monoclonal antibody were produced. Three IgG and IgM monoclonal antibodies that bound the *C. albicans* native β-mannan antigen were selected and these showed activity in in-vivo mouse protection studies.[15]

We claim:

1. A synthetic conjugate that is an oligosaceharide selected from the group consisting of [β-D-mannopyranose-(1→2)-β-D-mannopyranose-(1→2)-β-D-mannopyranose and β-D-mannopyranose-(1→2)-β-D-mannopyranose, wherein each saccharide unit of said oligosaccharide is linked via an inter-glycosidic atom selected from the group consisting of oxygen and sulfur; and wherein the oligosaccharide is covalently conjugated to a protein carrier through a linking group.

2. The conjugate of claim 1, wherein the oligosacehande is β-D-mannopyranose-(1→2)-β-D-mannopyranose-(1→2)-β-D-mannopyranose.

3. The conjugate of claim 1, wherein the oligosaceharide is β-D-mannopyranose-(1→2)-β-D-mannopyranose.

4. The conjugate of claim 1, wherein at least one inter-glycosidic atom is sulfur.

5. The conjugate of claim 4, wherein the inter-glycosidic atom at a terminal non-reducing end of at least one of the saccharide units is sulfur.

6. The conjugate of claim 1, wherein the linking group is derived from diethyl squarate, polyoxyalkylene, succinic anhydride or maleic anhydride.

7. The conjugate of claim 1, wherein the linking group is derived from a heterobifunctional or homobifunctional cross coupling reagent.

8. The conjugate of claim 1, wherein the linking group is derived from a mammalian lipid mimic or a bacterial lipid mimic wherein the mammalian lipid mimic or a bacterial lipid mimic is functionalized to permit covalent attachment to a protein or peptide carrier.

9. The conjugate of claim 8, wherein the mammalian lipid mimic or a bacterial lipid mimic is selected from the group consisting of sphingosine, a diacyl glycerol, and a diphytanyl ether of glycerol.

10. The conjugate of claim 1, wherein the protein carrier is selected from the group consisting of bovine serum albumin, human serum albumin, tetanus toxoid, a recombinant outer membrane class 3 porin (rPorB) from group B *Neisseria meningitidis*, and peptide carriers such as PADRE.

11. The conjugate of claim 10, wherein the protein carrier is tetanus toxoid or bovine serum albumin.

* * * * *

UNITED STATES PATENT AND TRADEMARK OFFICE
CERTIFICATE OF CORRECTION

PATENT NO. : 7,722,890 B2  Page 1 of 1
APPLICATION NO. : 10/512216
DATED : May 25, 2010
INVENTOR(S) : David R Bundle et al.

It is certified that error appears in the above-identified patent and that said Letters Patent is hereby corrected as shown below:

IN THE SPECIFICATION

In Column 13, Claim 1, Line 7, please replace "oligosaceharide" with -- oligosaccharide --.

In Column 13, Claim 2, Line 15, please replace "oligosacehande" with -- oligosaccharide --.

In Column 13, Claim 3, Line 18, please replace "oligosaceharide" with -- oligosaccharide --.

In Column 14, after Claim 11, Line 23, please insert Claim -- 12. The conjugate of any one of claims 1 or 3-12, wherein the *Candida* species is *Candida albicans*. --.

Signed and Sealed this

Fourteenth Day of December, 2010

David J. Kappos
*Director of the United States Patent and Trademark Office*